US010045930B2

(12) United States Patent
Viala et al.

(10) Patent No.: US 10,045,930 B2
(45) Date of Patent: Aug. 14, 2018

(54) DECORATIVE COSMETIC COMPOSITIONS

(75) Inventors: Sophie Viala, Cologne (DE); Sebastian Doerr, Duesseldorf (DE); Steffen Hofacker, Odenthal (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 28 days.

(21) Appl. No.: 12/934,763

(22) PCT Filed: Mar. 13, 2009

(86) PCT No.: PCT/EP2009/001817
§ 371 (c)(1),
(2), (4) Date: Dec. 21, 2010

(87) PCT Pub. No.: WO2009/118106
PCT Pub. Date: Oct. 1, 2009

(65) Prior Publication Data
US 2011/0097289 A1  Apr. 28, 2011

(30) Foreign Application Priority Data

Mar. 26, 2008  (EP) .................................... 08153273

(51) Int. Cl.
*A61K 8/87* (2006.01)
*A61Q 1/02* (2006.01)
*A61Q 19/00* (2006.01)
*A61Q 1/06* (2006.01)
*A61Q 1/10* (2006.01)
*A61Q 19/04* (2006.01)

(52) U.S. Cl.
CPC .................. *A61K 8/87* (2013.01); *A61Q 1/02* (2013.01); *A61Q 19/00* (2013.01); *A61Q 1/06* (2013.01); *A61Q 1/10* (2013.01); *A61Q 19/04* (2013.01)

(58) Field of Classification Search
CPC .......... A61K 8/87; A61Q 19/00; A61Q 19/04; A61Q 1/02; A61Q 1/06; A61Q 1/10
See application file for complete search history.

(56) References Cited

U.S. PATENT DOCUMENTS

| | | | |
|---|---|---|---|
| 5,612,397 A * | 3/1997 | Gebhard et al. ................ 524/35 |
| 5,650,159 A * | 7/1997 | Lion ........................ A61K 8/87 424/401 |
| 5,961,906 A | 10/1999 | Mueller et al. | |
| 5,972,354 A | 10/1999 | de la Poterie et al. | |
| 6,262,176 B1 | 7/2001 | Kim et al. | |
| 6,335,003 B1 | 1/2002 | Kim et al. | |
| 6,375,941 B1 | 4/2002 | Piot et al. | |
| 6,767,968 B1 | 7/2004 | Laas et al. | |
| 7,445,770 B2 * | 11/2008 | Berezkin et al. ................ 424/59 |
| 2002/0076425 A1 * | 6/2002 | Mondet et al. ................ 424/401 |
| 2002/0192168 A1 * | 12/2002 | Blin .................... A61K 8/4973 424/61 |
| 2003/0113285 A1 * | 6/2003 | Meffert et al. ............. 424/70.12 |
| 2004/0141942 A1 * | 7/2004 | Rollat ....................... A61K 8/87 424/70.17 |
| 2004/0197293 A1 | 10/2004 | Mougin | |
| 2005/0222368 A1 * | 10/2005 | Reiners .............. C08G 18/0823 528/73 |
| 2007/0025497 A1 | 2/2007 | Fujita | |
| 2007/0025943 A1 | 2/2007 | Patel | |
| 2007/0154440 A1 | 7/2007 | Fleissman et al. | |
| 2007/0184001 A1 * | 8/2007 | Vrignaud et al. ............ 424/70.2 |
| 2007/0243149 A1 * | 10/2007 | Hofacker ............... A61K 8/731 424/61 |
| 2007/0254974 A1 * | 11/2007 | Mager et al. ................. 521/172 |
| 2008/0039593 A1 * | 2/2008 | Glockner et al. ............. 525/450 |

FOREIGN PATENT DOCUMENTS

| | | |
|---|---|---|
| DE | 1954090 A1 | 5/1971 |
| DE | 4241118 A1 | 6/1994 |
| DE | 4241118 A1 | 6/1994 |
| DE | 69621104 T2 | 9/2002 |
| EP | 0636361 A1 | 2/1995 |
| EP | 0647667 A1 | 4/1995 |
| EP | 0775483 A1 | 5/1997 |
| EP | 0957119 A1 | 11/1999 |
| EP | 0957119 A1 | 11/1999 |
| EP | 1010418 A1 | 6/2000 |
| FR | 2832058 A1 | 5/2003 |
| GB | 1462597 A | 1/1977 |
| GB | 1462597 A | 1/1977 |
| WO | 9508583 A1 | 3/1995 |
| WO | 9939688 A2 | 8/1999 |
| WO | WO-99/39688 A2 | 8/1999 |
| WO | WO-01/88006 A1 | 11/2001 |
| WO | 0208327 A1 | 1/2002 |
| WO | WO-02/08327 A1 | 1/2002 |
| WO | 0209658 A1 | 2/2002 |
| WO | WO-02/09658 A1 | 2/2002 |
| WO | WO-02/070577 A1 | 9/2002 |
| WO | WO-2003/039445 A2 | 5/2003 |
| WO | WO 2006/076974 * | 7/2006 |
| WO | 2006/124250 A1 | 11/2006 |
| WO | 2007084596 A2 | 7/2007 |
| WO | WO-2007/084596 A2 | 7/2007 |
| WO | 2007115697 A1 | 10/2007 |
| WO | WO-2007/115697 A1 | 10/2007 |
| WO | 2008039466 A1 | 4/2008 |
| WO | WO-2008/039466 A1 | 4/2008 |

OTHER PUBLICATIONS

Pigment [online] retrieved from: http://www.merriam-webster.com/dictionary/pigment on Nov. 15, 2012; 4 pages.*

(Continued)

*Primary Examiner* — Mark V Stevens
(74) *Attorney, Agent, or Firm* — K&L Gates LLP

(57) ABSTRACT

The present invention relates to decorative cosmetic compositions comprising special polyurethanes or aqueous dispersions thereof and constituents providing decorative effects.

18 Claims, No Drawings

(56) References Cited

OTHER PUBLICATIONS

U.S. Appl. No. 12/934,519, filed Sep. 24, 2010.
U.S. Appl. No. 12/934,849, filed Sep. 27, 2010.
U.S. Appl. No. 12/934,539, filed Sep. 24, 2010.
Office Action for European Patent Application No. 09726012.9 dated Jan. 27, 2016.
European Search Report for European Patent Application No. 08153273 dated Sep. 8, 2008.

* cited by examiner

DECORATIVE COSMETIC COMPOSITIONS

RELATED APPLICATIONS

This application is a national stage application (under 35 U.S.C. § 371) of PCT/EP2009/001817, filed Mar. 13, 2009, which claims benefit of European Application No. 08153273.1, filed Mar. 26, 2008.

The present invention relates to decorative cosmetic compositions comprising special polyurethanes or aqueous dispersions thereof and constituents providing decorative effects.

A decorative cosmetic composition like that of the invention serves for the decorative, in particular colour, dressing of the human skin, mucosa, semimucosa and the hair, in particular the eyelids and the eyebrows. The decorative effect is achieved by at least one effect-imparting constituent. The decorative composition according to the invention can be, for example, a face make-up (foundation), a tinted (day)cream, a blusher, rouge, mascara, eyeliner, kohl pencil, eye shadow, lipstick, lip gloss. These special cosmetic formulations are used for changing the colour or for making up the body, in order, for example, to conceal rings around the eyes, an uneven complexion or other shortcomings of the skin, such as redness, marks, wrinkles or spots and thus to give the user a more aesthetic appearance. The list of decorative products given above is of course not limiting. Nail varnish compositions are excluded from this application.

The decorative cosmetic compositions expediently comprise one or more dyes, which are selected, for example, from the group of soluble dyes, inorganic pigments, such as, for example, iron oxides, chromium oxides, ultramarine, manganese violet, organic pigments and mother of pearl. Depending on the formulations, such decorative cosmetic compositions can consist of up to 80% of dyes and fillers, based on the total weight of the composition.

When using decorative cosmetic formulations, consumers naturally want a long-lasting decorative effect. In particular, consumers expect good resistance towards water, such as during bathing or showering, tears or perspiration, such as, in particular, during sporting activities.

In order to improve the resistance of decorative products towards water, tears or perspiration (often called water resistance), use is made of film-forming polymers. The film-forming polymers chosen are preferably polymers based on acrylates or vinylpyrrolidones. The disadvantages of such film-forming polymers are known to the person skilled in the art. The acrylate polymers form hard and brittle films. This results in an unpleasant feel when wearing the product. On account of the sticky skin feel, the vinylpyrrolidones can only be used in limited concentrations.

The use of polyurethane dispersions is also known in decorative cosmetics. Thus, US 2007/0154440 describes the use of a film-forming polyurethane with a molecular weight of at least 50000 in a cosmetic formulation for producing a long-lasting film on the skin. FR 2832058 describes the use of an aqueous polyurethane dispersion in an eyeliner composition. US 20070025943 describes the combination of a film-forming (meth)acrylate copolymer and a film-forming polyurethane in a cosmetic composition. EP 0775483 (DE 69621104) describes the use of an aqueous dispersion of synthetic, film-forming polymer particles in a composition for making up the lips. EP 1010418 describes the use of an aqueous polyurethane dispersion in a wax-free mascara composition. WO 2003039445 describes the use of an aqueous polyurethane dispersion in a cosmetic composition. WO02070577A1 (US 2004/0197293) describes anionic polyurethanes which can be used in cosmetic compositions. Specific examples of cosmetic compositions, however, are not described. The described anionic polyurethanes have a comparatively low water resistance and form aqueous polyurethane dispersions of comparatively high viscosity, which hinders their processing.

Wear comfort, in particular reduced stickiness, resistance, in particular water resistance, and lustre of the polyurethane-containing cosmetic compositions, in particular for the provision of decorative effects, from the prior art thus still have room for improvements. Furthermore, the aqueous polyurethane dispersions used in the prior art often have a disadvantageously high viscosity, which can hinder their processability and their incorporability into cosmetic formulations.

The object of the present invention was therefore to provide a decorative cosmetic composition which has a high wear comfort, in particular reduced stickiness, high resistance, in particular water resistance, and improved lustre properties. Furthermore, the aqueous polyurethane dispersions used according to the invention should have a comparatively low viscosity so that they can be readily incorporated into cosmetic compositions for decorative purposes.

Surprisingly, the object is achieved through the use of special polyurethanes or aqueous dispersions thereof, obtainable by reacting one or more water-insoluble, non-water-dispersible, isocyanate-functional polyurethane prepolymers A) with one or more amino-functional compounds B).

The present invention thus provides a decorative cosmetic composition comprising at least one polyurethane obtainable by reacting one or more water-insoluble, non-water-dispersible, isocyanate-functional polyurethane prepolymers A) with one or more amino-functional compounds B).

Furthermore, the present invention provides a decorative cosmetic composition comprising at least one polyurethane obtainable by reacting one or more isocyanate-functional polyurethane prepolymers A) which have essentially neither ionic nor ionogenic groups, with one or more amino-functional compounds B).

Within the context of the invention, the term "water-insoluble, non-water-dispersible polyurethane prepolymer" means in particular that the solubility in water of the prepolymer used according to the invention at 23° C. is less than 10 g/liter, more preferably less than 5 g/liter, and the prepolymer does not produce a sedimentation-stable dispersion in water, in particular deionized water, at 23°.

In other words, the prepolymer settles out upon attempting to disperse it in water.

Preferably, the polyurethane prepolymer A) used according to the invention has terminal isocyanate groups, i.e. the isocyanate groups are at the chain ends of the prepolymer. All of the chain ends of a polymer particularly preferably have isocyanate groups.

Furthermore, the polyurethane prepolymer A) used according to the invention preferably has essentially neither ionic nor ionogenic (capable of forming ionic groups) groups, i.e. the content of ionic and ionogenic groups is expediently below 15 milliequivalents per 100 g of polyurethane prepolymer A), preferably below 5 milliequivalents, particularly preferably below 1 milliequivalent and very particularly preferably below 0.1 milliequivalent per 100 g of polyurethane prepolymer A).

The amino-functional compounds B) are preferably selected from primary and/or secondary amines and/or diamines. In particular, the amino-functional compounds B)

include at least one diamine. The amino-functional compounds B) are preferably selected from amino-functional compounds B2), which have ionic or ionogenic group, and amino-functional compounds B1), which have no ionic or ionogenic group.

In a particularly preferred embodiment of the invention, the amino-functional compounds B) include at least one amino-functional compound B2) which has ionic and/or ionogenic (ion-forming) groups. The ionic and/or ionogenic group used is particularly preferably the sulphonate or the sulphonic acid group, yet more preferably the sodium sulphonate group.

In a further preferred embodiment of the invention, the amino-functional compounds B) include both amino-functional compounds B2) which have ionic and/or ionogenic group, and also amino-functional compounds B1) which have no ionic or ionogenic group.

Accordingly, polyurethanes within the context of the invention are polymeric compounds which have at least two, preferably at least three, repeat units containing urethane groups:

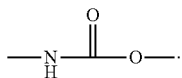

According to the invention, also included are those polyurethanes which, as a result of the preparation, also have repeat units containing urea groups:

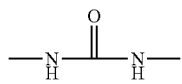

as are formed in particular in the reaction of the isocyanate-terminated prepolymers A) with the amino-functional compounds B).

The decorative cosmetic compositions according to the invention may be water-containing, i.e. aqueous compositions in which the polyurethane is present in dispersed form, i.e. essentially not in dissolved form. Besides any other liquid media which may be present, such as, for example, solvents, water can be the main constituent (>50% by weight) of the dispersion media, based on the total amount of the liquid dispersion media in the cosmetic compositions according to the invention, and in some cases can also be the sole liquid dispersion medium.

The decorative cosmetic compositions according to the invention preferably have a content of volatile organic compounds (VOCs) of less than 80% by weight, more preferably of less than 55% by weight, even more preferably of less than 40% by weight, based on the decorative cosmetic composition.

The aqueous polyurethane dispersions used for the preparation of the decorative cosmetic compositions according to the invention preferably have a content of volatile organic compounds (VOCs) of less than 10% by weight, more preferably of less than 3% by weight, even more preferably of less than 1% by weight, based on the aqueous polyurethane dispersion.

The content of volatile organic compounds (VOCs) is determined within the context of the present invention in particular by gas chromatographic analysis.

The non-water-soluble and non-water-dispersible, isocyanate-functional polyurethane polymers used according to the invention have essentially neither ionic nor ionogenic groups. The insolubility in water and/or lack of dispersibility in water refers to deionized water without the addition of surfactants. Within the context of the present invention this means that the proportion of ionic and/or ionogenic (ion-forming) groups, such as, in particular, anionic groups, such as carboxylate or sulphonate, or of cationic groups is less than 15 milliequivalents per 100 g of polyurethane prepolymer A), preferably less than 5 milliequivalents, particularly preferably less than 1 milliequivalent and very particularly preferably less than 0.1 milliequivalent per 100 g of polyurethane prepolymer A).

In the case of acidic ionic and/or ionogenic groups, the acid number of the prepolymer is expediently below 30 mg of KOH/g of prepolymer, preferably below 10 mg of KOH/g of prepolymer. The acid number indicates the mass of potassium hydroxide in mg which is required to neutralize 1 g of the sample under investigation (measurement in accordance with DIN EN ISO 211). The neutralized acids, i.e. the corresponding salts, naturally have no acid number or a reduced acid number. According to the invention, the acid number of the corresponding free acid is decisive here.

The prepolymers A) used for the preparation of the polyurethanes are preferably obtainable by reacting one or more polyols selected from the group which consists of polyether polyols, polycarbonate polyols, polyether polycarbonate polyols and/or polyester polyols, and polyisocyanates, as is explained in more detail below.

The polyurethanes present in the decorative cosmetic compositions according to the invention accordingly comprise, via the prepolymer A), preferably at least one sequence selected from the group which consists of: polyether, polycarbonate, polyether-polycarbonate and polyester sequences. According to the invention, this means in particular that the polyurethanes contain repeat units containing ether groups and/or carbonate groups or ester groups. The polyurethanes can contain, for example, exclusively polyether sequences or exclusively polycarbonate sequences or exclusively polyester sequences. However, they can also have both polyether and polycarbonate sequences, as are formed, for example, during the preparation of polycarbonate polyols using polyetherdiols, as is described in more detail below. In addition, they can have polyether-polycarbonate sequences which arise from the use of polyether-polycarbonate polyols, as described in more detail below.

Particularly preferred polyurethanes are obtained using polymeric polyether polyols and/or polymeric polycarbonate polyols and/or polyether-polycarbonate polyols or polyester polyols, each of which have number-average molecular weights of preferably about 400 to about 6000 g/mol (here and in the case of the molecular weight data below, determined by gel permeation chromatography relative to polystyrene standard in tetrahydrofuran at 23° C.). Their use during the preparation of the polyurethanes or polyurethane prepolymers leads, as a result of reaction with polyisocyanates, to the formation of corresponding polyether and/or polycarbonate and/or polyether-polycarbonate sequences or polyester sequences in the polyurethanes with a corresponding molecular weight of these sequences. According to the invention, particular preference is given to polyurethanes which are obtained from polymeric polyetherdiols and/or polymeric polycarbonatediols and/or polyether-polycarbonate polyols or polyester polyols with a linear structure.

The polyurethanes according to the invention are preferably essentially linear molecules, but may also be branched, which is less preferred.

The number-average molecular weight of the polyurethanes preferably used according to the invention is, for example, about 1000 to 200 000, preferably from 500 to 150 000.

The polyurethanes present in the decorative cosmetic compositions according to the invention are added to the specified compositions in particular in the form of aqueous dispersions.

Preferred polyurethanes or polyurethane dispersions to be used according to the invention are obtainable by preparing
A) isocyanate-functional prepolymers of
  A1) organic polyisocyanates,
  A2) polymeric polyols, preferably with number-average molecular weights of from 400 to 8000 g/mol (here and for the molecular weight data below, determined by gel permeation chromatography relative to polystyrene standard in tetrahydrofuran at 23° C.), more preferably 400 to 6000 g/mol and particularly preferably from 600 to 3000 g/mol, and OH functionalities of preferably 1.5 to 6, more preferably 1.8 to 3, particularly preferably from 1.9 to 2.1,
  A3) optionally hydroxy-functional compounds with molecular weights of preferably 62 to 399 g/mol, and
  A4) optionally nonionic hydrophilizing agents, and
B) then reacting some or all of their free NCO groups with one or more amino-functional compounds B), such as primary and/or secondary amines and/or diamines.

The polyurethanes used according to the invention are preferably dispersed in water before, during or after step B).

The reaction with a diamine or two or more diamines in step B) particularly preferably takes place with chain extension. In this connection, monofunctional amines can additionally be added as chain terminators to control the molecular weight.

As component B), in particular amines can be used which have no ionic or ionogenic, such as anionically hydrophilizing groups (component B1 below)) and it is possible to use amines which have ionic or ionogenic, such as, in particular, anionically hydrophilizing groups (component B2 below)).

Preferably, in step B) of the reaction of the prepolymer, a mixture of component B1) and component B2) is reacted. By using component B1) it is possible to build up a high molar mass without the viscosity of the previously prepared isocyanate-functional prepolymer increasing to a degree which would be an obstacle to processing. By using the combination of components B1) and B2) it is possible to achieve an optimum balance between hydrophilicity and chain length and thus establish a pleasant skin feel.

The polyurethanes used according to the invention preferably have anionic groups, preferably sulphonate groups. These anionic groups are introduced into the polyurethanes used according to the invention via the amine component B2) reacted in step B). The polyurethanes used according to the invention optionally additionally have nonionic components for hydrophilization. Exclusively sulphonate groups are particularly preferably present in the polyurethanes used according to the invention for the hydrophilization; these are introduced into the polyurethane via corresponding diamines as component B2).

In order to achieve a good sedimentation stability, the number-average particle size of the special polyurethane dispersions is preferably less than 750 nm, particularly preferably less than 500 nm, determined by means of laser correlation spectroscopy following dilution with deionized water (instrument: Malvern Zetasizer 1000, Malvern Inst. Limited).

The solids content of the polyurethane dispersions which is preferably used for preparing the decorative cosmetic composition of the invention is generally 10 to 70% by weight, preferably 30 to 65% by weight, particularly preferably 40 to 60% by weight. The solids contents are ascertained by heating a weighed sample at 125° C. to constant weight. At constant weight, the solid-body content is calculated by reweighing the sample.

Preferably, these polyurethane dispersions have less than 5% by weight, particularly preferably less than 0.2% by weight, based on the mass of the dispersions, of unbonded organic amines The content in the decorative cosmetic compositions is correspondingly yet lower.

Suitable polyisocyanates of component A1) are in particular the aliphatic, aromatic or cycloaliphatic polyisocyanates with an NCO functionality of greater than or equal to 2 known per se to the person skilled in the art.

Examples of such suitable polyisocyanates are 1,4-butylene diisocyanate, 1,6-hexamethylene diisocyanate (HDI), isophorone diisocyanate (IPDI), 2,2,4- and/or 2,4,4-trimethylhexamethylene-diisocyanate, the isomeric bis(4,4'-isocyanatocyclohexyl)methanes or mixtures thereof of any desired isomer content, 1,4-cyclohexylene diisocyanate, 4-isocyanatomethyl-1,8-octane diisocyanate (nonane triisocyanate), 1,4-phenylene diisocyanate, 2,4- and/or 2,6-tolylene diisocyanate, 1,5-naphthylene diisocyanate, 2,2'- and/or 2,4'- and/or 4,4'-diphenylmethane diisocyanate, 1,3- and/or 1,4-bis(2-isocyanatoprop-2-yl)benzene (TMXDI), 1,3-bis(isocyanatomethyl)benzene (XDI), and alkyl 2,6-diisocyanatohexanoates (lysine diisocyanates) with C1-C8-alkyl groups.

Besides the aforementioned polyisocyanates, it is also possible to use modified diisocyanates which have a functionality of ≥2 with uretdione, isocyanurate, urethane, allophanate, biuret, iminooxadiazinedione or oxadiazinetrione structure, and also mixtures of these proportionately.

They are preferably polyisocyanates or polyisocyanate mixtures of the type specified above with exclusively aliphatically or cycloaliphatically bonded isocyanate groups or mixtures of these and an average NCO functionality of the mixture of from 2 to 4, preferably 2 to 2.6 and particularly preferably 2 to 2.4, very particularly preferably 2.

Hexamethylene diisocyanate, isophorone diisocyanate or the isomeric bis(4,4'-isocyanato-cyclohexyl)methanes, and mixtures of the aforementioned diisocyanates are particularly preferably used in A1).

In A2), polymeric polyols with a number-average molecular weight $M_n$ of preferably 400 to 8000 g/mol, more preferably from 400 to 6000 g/mol and particularly preferably from 600 to 3000 g/mol are used. These preferably have a OH functionality of from 1.5 to 6, particularly preferably from 1.8 to 3, very particularly preferably from 1.9 to 2.1.

The expression "polymeric" polyols means here in particular that the specified polyols have at least two, more preferably at least three, repeat units joined together.

Such polymeric polyols are the polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols known per se in polyurethane coating technology. These can be used in A2) individually or in any desired mixtures with one another.

The preferably used polyester polyols are the polycondensates known per se of di- and optionally tri- and tetraols and di- and optionally tri- and tetracarboxylic acids or hydroxycarboxylic acids or lactones. Instead of the free polycarboxylic acids, it is also possible to use the corresponding polycarboxylic acid anhydrides or corresponding polycarboxylic acid esters of lower alcohols for the preparation of the polyesters.

Examples of suitable diols are ethylene glycol, butylene glycol, diethylene glycol, triethylene glycol, polyalkylene glycols, such as polyethylene glycol, also 1,2-propanediol, 1,3-propanediol, butanediol(1,3), butanediol(1,4), hexanediol(1,6) and isomers, neopentyl glycol or hydroxypivalic neopentyl glycol ester, where hexanediol(1,6) and isomers, butanediol(1,4), neopentyl glycol and hydroxypivalic neopentyl glycol ester are preferred. In addition, polyols such as trimethylolpropane, glycerol, erythritol, pentaerythritol, trimethylolbenzene or trishydroxyethyl-isocyanurate can also be used.

Dicarboxylic acids which can be used are phthalic acid, isophthalic acid, terephthalic acid, tetra-hydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid. The corresponding anhydrides may also be used as acid source.

If the average functionality of the polyol to be esterified is > than 2, monocarboxylic acids, such as benzoic acid and hexane carboxylic acid, can additionally also be co-used.

Preferred acids are aliphatic or aromatic acids of the type specified above. Particular preference is given to adipic acid, isophthalic acid and phthalic acid.

Hydroxycarboxylic acids which can be co-used as reactants in the preparation of a polyester polyol with terminal hydroxyl groups are, for example, hydroxycaproic acid, hydroxybutyric acid, hydroxydecanoic acid, hydroxystearic acid and the like. Suitable lactones are caprolactone, butyrolactone and homologs. Preference is given to caprolactone.

According to the invention, particularly preferred components A2) for the preparation of the polyurethanes are polyester polyols with a number-average molecular weight of from 600 to 3000 g/mol, in particular aliphatic polyester polyols based on aliphatic carboxylic acids and aliphatic polyols, in particular based on adipic acid and aliphatic alcohols, such as hexanediol and/or neopentyl glycol.

Polycarbonates having hydroxyl groups, preferably polycarbonatediols, with number-average molecular weights $M_n$ of from preferably 400 to 8000 g/mol, preferably 600 to 3000 g/mol can likewise be used as component A2). These are obtainable by reacting carbonic acid derivatives, such as diphenyl carbonate, dimethyl carbonate or phosgene, with polyols, preferably diols.

Examples of such diols are ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentanediol-1,3, dipropylene glycol, polypropylene glycols, dibutylene glycol, polybutylene glycols, bisphenol A and lactone-modified diols of the type specified above.

Preferably, the diol component comprises 40 to 100% by weight of hexanediol, preference being given to 1,6-hexanediol and/or hexanediol derivatives. Such hexanediol derivatives are based on hexanediol and, besides terminal OH groups, have ester or ether groups. Such derivatives are obtainable by reacting hexanediol with excess caprolactone or by etherifying hexanediol with itself to give the di- or trihexylene glycol.

Instead of or in addition to the pure polycarbonatediols, it is also possible to use polyether-polycarbonatediols in A2).

Polycarbonates having hydroxyl groups preferably have a linear structure.

Polyether polyols can likewise be used as component A2).

For example, the polytetramethylene glycol polyethers known per se in polyurethane chemistry, as are obtainable through polymerization of tetrahydrofuran by means of cationic ring opening, are particularly suitable.

Likewise suitable polyether polyols are the addition products, known per se, of styrene oxide, ethylene oxide, propylene oxide, butylene oxide and/or epichlorohydrin onto di- or polyfunctional starter molecules. Thus, in particular polyalkylene glycols, such as polyethylene glycols, polypropylene glycols and/or polybutylene glycols, can be used, in particular those with the preferred molecular weights specified above.

Suitable starter molecules which can be used are all compounds known according to the prior art, such as, for example, water, butyl diglycol, glycerol, diethylene glycol, trimethylolpropane, propylene glycol, sorbitol, ethylenediamine, triethanolamine 1,4-butanediol.

Particularly preferred components in A2) are polytetramethylene glycol polyether and polycarbonate polyols and mixtures thereof and particularly preferably polytetramethylene glycol polyethers.

In preferred embodiments of the invention, component A2) is accordingly:
  mixtures comprising at least one polyether polyol and at least one polycarbonate polyol,
  mixtures comprising more than one polyether polyol, or a mixture of two or more polyether polyols with different molecular weights, which are in particular poly(tetramethylene glycol) polyether polyols (such as HO—$(CH_2$—$CH_2$—$CH_2$—$CH_2$—$O)_x$—H),
  mixtures comprising more than one polyether polyol and at least one polycarbonate polyol, and also
  particularly preferably polyester polyols with a number-average molecular weight of from 600 to 3000 g/mol, in particular aliphatic polyester polyols based on aliphatic carboxylic acids and aliphatic polyols, in particular based on adipic acid and aliphatic alcohols, such as hexanediol and/or neopentyl glycol,
where component A), according to the definition, has essentially neither ionic nor ionogenic groups.

As component A3), polyols, in particular nonpolymeric polyols, of the specified preferred molecular weight range from 62 to 399 mol/g with up to 20 carbon atoms, such as ethylene glycol, diethylene glycol, triethylene glycol, 1,2-propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenyl)propane), hydrogenated bisphenol A (2,2-bis(4-hydroxycyclohexyl) propane), trimethylolpropane, trimethylolethane, glycerol, pentaerythritol, and any mixtures thereof can be used as desired.

Also suitable are ester diols of the specified molecular weight range, such as α-hydroxybutyl ε-hydroxycaproic acid ester, ω-hydroxyhexyl γ-hydroxybutyric acid ester, adipic acid (β-hydroxy-ethyl) ester or terephthalic acid bis(β-hydroxyethyl) ester.

In addition, as component A3), it is also possible to use monofunctional isocyanate-reactive hydroxyl-group-containing compounds. Examples of such monofunctional compounds are ethanol, n-butanol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

In one preferred embodiment of the invention, the polyurethane used according to the invention comprises less than about 10% by weight of component A3), preferably less than 5% by weight of component A3), in each case based on the total mass of the polyurethane, yet more preferably component A3) is not used for the preparation of the polyurethane.

To prepare the polyurethanes used according to the invention, one or more in particular isocyanate-reactive nonionic hydrophilizing agents are optionally used as component A4). The hydrophilizing agents used as component A4) are in particular different from components A2) and A3).

Suitable nonionically hydrophilizing compounds as component A4) are, for example, polyoxyalkylene ethers which have isocyanate-reactive groups, such as hydroxy, amino or thiol groups. Preference is given to monohydroxy-functional polyalkylene oxide polyether alcohols having, on statistical average, 5 to 70, preferably 7 to 55, ethylene oxide units per molecule, as are accessible in a manner known per se by alkoxylation of suitable starter molecules (e.g. in Ullmanns Encyclopädie der technischen Chemie [Ullmanns encyclopaedia of industrial chemistry], 4th edition, Volume 19, Verlag Chemie, Weinheim pp. 31-38). These are either pure polyethylene oxide ethers or mixed polyalkylene oxide ethers, where they contain at least 30 mol %, preferably at least 40 mol %, ethylene oxide units, based on all of the alkylene oxide units present.

Particularly preferred nonionic compounds are monofunctional mixed polyalkylene oxide polyethers which have 40 to 100 mol % ethylene oxide units and 0 to 60 mol % propylene oxide units.

Suitable starter molecules for such nonionic hydrophilizing agents are in particular saturated monoalcohols, such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, such as, for example, diethylene glycol monobutyl ether, unsaturated alcohols, such as allyl alcohol, 1,1-dimethylallyl alcohol or oleyl alcohol, aromatic alcohols, such as phenol, the isomeric cresols or methoxyphenols, araliphatic alcohols, such as benzyl alcohol, anisyl alcohol or cinnamyl alcohol, secondary monoamines, such as dimethylamine, diethylamine, dipropylamine, diisopropylamine, dibutylamine, bis(2-ethylhexyl)amine, N-methyl- and N-ethylcyclohexylamine or dicyclohexylamine, and also heterocyclic secondary amines, such as morpholine, pyrrolidine, piperidine or 1H-pyrazole. Preferred starter molecules are saturated monoalcohols of the type specified above. Particular preference is given to using diethylene glycol monobutyl ether or n-butanol as starter molecules.

Alkylene oxides suitable for the alkoxylation reaction are in particular ethylene oxide and propylene oxide, which can be used in the alkoxylation reaction in any desired order or else in a mixture.

Component B) is preferably selected from primary or secondary amine and/or diamines. It includes in particular diamines.

As component B) it is possible to use in particular amines which have no ionic or ionogenic, such as anionically hydrophilizing groups (component B1) below), and it is possible to use amines which have ionic or ionogenic, such as, in particular, anionically hydrophilizing groups (component B2) below). Preferably, in step B) of the reaction of the prepolymer, a mixture of component B1) and of component B2) is reacted.

For example, organic di- or polyamines, such as, for example, 1,2-ethylenediamine, 1,2- and 1,3-diaminopropane, 1,4-diaminobutane, 1,6-diaminohexane, isophoronediamine, isomer mixture of 2,2,4- and 2,4,4-trimethylhexamethylenediamine, 2-methylpentamethylenediamine, diethylenetriamine, 4,4-diaminodicyclohexylmethane, hydrazine hydrate, and/or dimethylethylenediamine, can be used as component B1).

Moreover, compounds which, besides a primary amino group, also have secondary amino groups or, besides an amino group (primary or secondary), also have OH groups, can also be used as component B1). Examples thereof are primary/secondary amines, such as diethanolamine, 3-amino-1-methyl aminopropane, 3-amino-1-ethylaminopropane, 3-amino-1-cyclohexylaminopropane, 3-amino-1-methylaminobutane, alkanolamines, such as N-aminoethylethanolamine, ethanolamine, 3-aminopropanol, neopentanolamine.

In addition, monofunctional isocyanate-reactive amine compounds can also be used as component B1), such as, for example, methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl) aminopropylamine, morpholine, piperidine, and suitable substituted derivatives thereof, amidoamines of diprimary amines and monocarboxylic acids, monoketime of diprimary amines, primary/tertiary amines, such as N,N-di-methylaminopropylamine.

As component B1), preference is given to using 1,2-ethylenediamine, bis(4-aminocyclohexyl)methane, 1,4-diaminobutane, isophoronediamine, ethanolamine, diethanolamine and diethylenetriamine.

Component B) particularly preferably includes at least one component B2). Suitable anionically hydrophilizing compounds as component B2) preferably contain a sulphonic acid or sulphonate group, particularly preferably a sodium sulphonate group. Suitable anionically hydrophilizing compounds as component B2) are, in particular, the alkali metal salts of mono- and diaminosulphonic acids. Examples of such anionic hydrophilizing agents are salts of 2-(2-aminoethylamino)ethanesulphonic acid, ethylenediamine-propyl- or -butylsulphonic acid, 1,2- or 1,3-propylenediamine-B-ethylsulfonic acid or taurine. Furthermore, the salt of cyclohexylaminopropanesulphonic acid (CAPS) from WO-A 01/88006 can be used as anionic hydrophilizing agent.

Particularly preferred anionic hydrophilizing agents B2) are those which contain sulphonate groups as ionic groups and two amino groups, such as the salts of 2-(2-aminoethylamino)ethylsulphonic acid and 1,3-propylenediamine-β-ethylsulfonic acid.

The polyurethanes used according to the invention particularly preferably comprise at least one sulphonate group.

Optionally, the anionic group in component B2) may also be a carboxylate or carboxylic acid group. Component B2)

is then preferably selected from diaminocarboxylic acids. However, this embodiment is less preferred since carboxylic-acid-based components B2) have to be used in higher concentrations.

For the hydrophilization, it is also possible to use mixtures of anionic hydrophilizing agents B2) and nonionic hydrophilizing agents A4).

In a preferred embodiment for the preparation of the special polyurethane dispersions, components A1) to A4) and B1) to B2) are used in the following amounts, the individual amounts always adding up to 100% by weight:
5 to 40% by weight of component A1),
55 to 90% by weight of A2),
0.5 to 20% by weight sum of components A3) and/or B1),
0.1 to 25% by weight sum of components A4) and/or B2),
where, based on the total amounts of components A1) to A4) and B1) to B2), particularly preferably 0.1 to 5% by weight of anionic or potentially anionic hydrophilizing agents B2) are used.

In a particularly preferred embodiment for the preparation of the special polyurethane dispersions, components A1) to A4) and B1) to B2) are used in the following amounts, the individual amounts always adding up to 100% by weight:
5 to 35% by weight of component A1),
60 to 90% by weight of A2),
0.5 to 15% by weight sum of components A3) and/or B1),
0.1 to 15% by weight sum of components A4) and/or B2),
where, based on the total amounts of components A1) to A4) and B1) to B2), particularly preferably 0.2 to 4% by weight of anionic or potentially anionic hydrophilizing agents B2) are used.

In a very particularly preferred embodiment for the preparation of the special polyurethane dispersions, components A1) to A4) and B1) to B2) are used in the following amounts, the individual amounts always adding up to 100% by weight:
10 to 30% by weight of component A1),
65 to 85% by weight of A2),
0.5 to 14% by weight sum of components A3 and/or B1),
0.1 to 13.5% by weight sum of components A4) and/or B2),
where, based on the total amounts of components A1) to A4) and B1) to B2), particularly preferably 0.5 to 3.0% by weight of anionic or potentially anionic hydrophilizing agents from B2) are used.

The preparation of the polyurethane dispersions can be carried out in one or more stage(s) in homogeneous phase or, in the case of multistage reaction, sometimes in disperse phase. Following complete or partial polyaddition from A1) to A4), a dispersion, emulsification or dissolution step preferably takes place. Afterwards, a further polyaddition or modification optionally takes place in the disperse phase.

In this connection, all of the methods known from the prior art, such as, for example, prepolymer mixing process, acetone process or melt dispersion process, can be used. Preference is given to using the acetone process.

For the preparation in accordance with the acetone process, constituents A2) to A4) and the polyisocyanate component A1) for the preparation of an isocyanate-functional polyurethane prepolymer are usually initially introduced in their entirety or in part and optionally diluted with a solvent which is miscible with water but inert towards isocyanate groups, and heated to temperatures in the range from 50 to 120° C. To increase the rate of the isocyanate addition reaction, the catalysts known in polyurethane chemistry can be used.

Suitable solvents are the customary aliphatic, keto-functional solvents such as acetone, 2-butanone, which can be added not only at the start of the preparation, but optionally in parts also later on. Preference is given to acetone and 2-butanone, and particular preference is given to acetone. The addition of other solvents without isocyanate-reactive groups is also possible, but not preferred.

Any constituents of A1) to A4) not added at the start of the reaction are then metered in.

During the preparation of the polyurethane prepolymer from A1) to A4), the quantitative ratio of isocyanate groups to isocyanate-reactive groups is generally 1.05 to 3.5, preferably 1.1 to 3.0, particularly preferably 1.1 to 2.5.

The reaction of components A1) to A4) to give the prepolymer takes place partially or completely, but preferably completely. Polyurethane prepolymers which contain free isocyanate groups are thus obtained without a diluent or in solution.

In the neutralization step for the partial or complete conversion of potentially anionic groups to anionic groups, bases such as tertiary amines, e.g. trialkylamines having 1 to 12, preferably 1 to 6, carbon atoms, particularly preferably 2 to 3 carbon atoms in each alkyl radical or very particularly preferably alkali metal bases such as the corresponding hydroxides are used.

The use of organic amines is not preferred.

Neutralizing agents which can be used are preferably inorganic bases, such as aqueous ammonia solution or sodium hydroxide or potassium hydroxide.

Preference is given to sodium hydroxide and potassium hydroxide.

The quantitative amount of the bases is 50 and 125 mol %, preferably between 70 and 100 mol % of the quantitative amount of the acid groups to be neutralized. The neutralization can also take place at the same time as the dispersion by the dispersion water already comprising the neutralizing agent.

Afterwards, in a further process step, in cases where it has still not happened or has only happened partially, the resulting prepolymer is dissolved with the help of aliphatic ketones such as acetone or 2-butanone.

The reaction of components A1) to A4) to give the prepolymer takes place partially or completely, but preferably completely. In this way, polyurethane prepolymers which contain free isocyanate groups are obtained without a diluent or in solution.

During the chain extension in stage B), $NH_2$- and/or NH-functional components are reacted with the remaining isocyanate groups of the prepolymer. Preferably, the chain extension/termination is carried out prior to the dispersion in water.

Suitable components B) for the chain extension are, in particular, organic di- or polyamines B1), such as, for example, ethylenediamine, 1,2- and 1,3-diaminopropane, 1,4-diaminobutane, 1,6-diaminohexane, isophoronediamine, isomer mixture of 2,2,4- and 2,4,4-trimethylhexamethylenediamine, 2-methylpentamethylenediamine, diethylenetriamine, diaminodicyclohexylmethane and/or dimethylethylenediamine.

Moreover, it is also possible to use compounds B1) which, besides a primary amino group, also have secondary amino groups or, besides an amino group (primary or secondary), also have OH groups. Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, alkanolamines, such as N-aminoethylethanolamine, ethanolamine, 3-aminopropanol, neopentanolamine to be used for the chain extension and/or termination.

For the chain termination, use is usually made of amines B1) having a group which is reactive towards isocyanates, such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, and suitable substituted derivatives thereof, amidoamines of diprimary amines and monocarboxylic acids, monoketime of diprimary amines, primary/tertiary amines, such as N,N-dimethylaminopropylamine.

If anionic hydrophilizing agents corresponding to the definition of B2) with $NH_2$ or NH groups are used for the chain extension, the chain extension of the prepolymers preferably takes place before the dispersion.

The degree of chain extension, i.e. the equivalent ratio of NCO-reactive groups of the compounds used for the chain extension and chain termination to free NCO groups of the prepolymer is generally between 40 and 150%, preferably between 50 and 110%, particularly preferably between 60 and 100%.

The aminic components B1) and B2) can optionally be used in water- or solvent-diluted form in the process according to the invention individually or in mixtures, with any order of the addition being possible in principle.

If water or organic solvents are co-used as diluents, then the diluent content in the component used in B) for the chain extension is preferably 40 to 95% by weight.

The dispersion preferably takes place after the chain extension. For this, the dissolved and chain-extended polyurethane polymer is optionally either introduced into the dispersion water with strong shear, such as, for example, vigorous stirring, or, conversely, the dispersion water is stirred into the chain-extended polyurethane polymer solutions. Preferably, the water is added to the dissolved chain-extended polyurethane polymer.

The solvent still present in the dispersions after the dispersion step is then usually removed by distillation. Removal during dispersion is likewise possible.

The residual content of organic solvents in the polyurethane dispersions prepared in this way is typically less than 10% by weight, preferably less than 3% by weight, based on the total dispersion.

The pH of the aqueous polyurethane dispersions used according to the invention is typically less than 8.0, preferably less than 7.5 and is particularly preferably between 5.5 and 7.5.

The decorative cosmetic composition according to the invention preferably comprises 0.1 to 20% by weight of the polyurethane described above and in particular 0.5 to 10% by weight, in each case based on the total weight of the composition.

The decorative cosmetic composition of the invention serves for the decorative, in particular colour or effect-imparting, dressing of the human skin, mucosa, semimucosa and the hair, in particular the eyelids and the eyebrows (generally not head hair). The decorative effect, i.e. colour effect or other effect (glitter effect, metallic effect etc.) is achieved by at least one effect-imparting, in particular colour- and/or effect-imparting constituent. The decorative composition according to the invention can be, for example, a face make-up (foundation), a tinted (day)cream, a blusher, a rouge, mascara, eyeliner, kohl pencil, eye shadow, lipstick, lip gloss. The decorative composition according to the invention does not include ones for application to nails, such as nail varnish in general. One characteristic of the decorative cosmetic compositions is generally that they are so-called "leave on" products which, following application, at least partially remain on the skin or the hair.

The decorative cosmetic composition according to the invention can in particular be solid, liquid or semisolid. The composition can be in the form of oil-in-water, water-in-oil, water-in-silicone oil, silicone oil-in-water, oil-in-water-in-oil, water-in-oil-in-water or solids emulsions (emulsions which are stabilized by solids, such as, for example, Pickering emulsions). The formulation according to the invention can also be foamed using a propellant gas. The formulation according to the invention can furthermore be in the form of loose powder, compact powder, mousse, sticks or in the form of the aforementioned liquid or viscous emulsions.

The composition according to the invention comprises at least one effect-imparting constituent. Said constituent may in particular be colour-imparting, but also provide other effects, such as glitter effects and/or metallic effects. Preferably, the composition according to the invention comprises at least one dye which is preferably selected from the group of lipophilic dyes, hydrophilic dyes, pigments and mother of pearl. According to the invention, the concentration of dyes is particularly advantageously 0.01 to 40% by weight, particularly advantageously 1.0 to 30% by weight, very particularly advantageously from 2.0 to 25% by weight, in each case based on the total weight of the composition.

For example, lipophilic dyes can be used, such as Sudan I (yellow), Sudan II (orange), Sudan III (red), Sudan IV (scarlet red), DC Red 17, DC Green 6, β-carotene, soybean oil, DC Yellow 11, DC Violet 2, DC Orange 5 and DC Yellow 10.

The pigments can in principle be all inorganic or organic pigments which are used in cosmetic or dermatological compositions. The pigments used according to the invention can, for example, be white or coloured, they can be coated with a hydrophobic treatment agent or be uncoated.

The pigments are advantageously selected from the group of metal oxides, such as the oxides of iron (in particular the oxides or yellow, red, brown, black colour), titanium dioxide, zinc oxide, cerium oxide, zirconium oxide, chromium oxide; manganese violet, ultramarine blue, Prussian blue, ultramarine and iron blue, bismuth oxychloride, mother of pearl, mica pigments, coated with titanium or bismuth oxychloride, coloured pearlescent pigments, for example titanium-mica pigments with iron oxides, titanium-mica pigments, in particular with iron blue or chromium oxide, titanium-mica pigments with an organic pigment of the aforementioned type, and also pearlescent pigments based on bismuth oxychloride, carbon black, the pigments of the type D & C and the lakes based on cochineal red, barium, strontium, calcium and aluminium and mixtures thereof.

The pigments of iron oxides or titanium dioxide are used particularly advantageously.

For better wettability of the pigments by the oils of the fatty phase, the surface of the pigments is preferably treated with a hydrophobic treatment agent. The hydrophobic treatment agent is preferably selected from the group of silicones, such as methicones, dimethicones, perfluoroalkylsilanes; fatty acids such as stearic acid; metal soaps, such as aluminium dimyristate, the aluminium salt of hydrogenated tallow glutamate, perfluoroalkyl phosphates, perfluoroalkylsilanes, perfluoroalkylsilazanes, hexafluoropropylene polyoxides, polyorganosiloxanes which contain perfluoroalkylperfluoropolyether groups, amino acids; N-acylated amino acids or salts thereof; lecithin, isopropyl triisostearyl titanate and mixtures thereof. The N-acylated amino acids that can contain an acyl group having 8 to 22 carbon atoms, for example 2-ethylhexanoyl, caproyl, lauroyl, myristoyl, palmitoyl, stearoyl or cocoyl. The salts of these compounds can be aluminium salts, magnesium salts, calcium salts, zirconium salts, tin salts, sodium salts or potassium salts. The amino acid may be, for example, lysine, glutamic acid or alanine.

The decorative cosmetic compositions according to the invention can comprise one or more emulsifiers or surface-active agents.

Thus, oil-in-water emulsions (O/W) according to the invention preferably comprise at least one emulsifier with an HLB value of >7 and optionally a coemulsifier.

The following nonionic emulsifiers are advantageously used:
- a) partial fatty acid esters and fatty acid esters of polyhydric alcohols and ethoxylated derivatives thereof (e.g. glyceryl monostearate, sorbitan stearate, glyceryl stearyl citrate, sucrose stearate)
- b) ethoxylated fatty alcohols and fatty acids.

Particularly advantageous non-ionic O/W emulsifiers are ethoxylated fatty alcohols or fatty acids, preferably PEG-100 stearate, PEG-40 stearate, ceteareth-20, ceteth-20, steareth-20, ceteareth-12, ceteth-12, steareth-12, and esters of mono-, oligo- or polysaccharides with fatty acids, preferably cetearyl glucoside, methyl glucose distearate.

Advantageous anionic emulsifiers are soaps (e.g. sodium or triethanolamine salts of stearic acid or palmitic acid), and also esters of citric acid, such as glyceryl stearate citrate.

Suitable coemulsifiers which can be used for the O/W emulsions according to the invention are fatty alcohols having 8 to 30 carbon atoms, monoglycerol esters of saturated or unsaturated, branched or unbranched alkanecarboxylic acids with a chain length of from 8 to 24 carbon atoms, in particular 12 to 18 carbon atoms, propylene glycol esters of saturated or unsaturated, branched or unbranched alkanecarboxylic acids with a chain length of from 8 to 24 carbon atoms, in particular 12 to 18 carbon atoms, and also sorbitan esters of saturated or unsaturated, branched or unbranched alkanecarboxylic acids with a chain length from 8 to 24 carbon atoms, in particular 12 to 18 carbon atoms.

Particularly advantageous coemulsifiers are glyceryl monostearate, glyceryl monooleate, diglyceryl monostearate, sorbitan monoisostearate, sucrose distearate, cetyl alcohol, stearyl alcohol, behenyl alcohol, isobehenyl alcohol and polyethylene glycol(2) stearyl ether (steareth-2).

Within the context of the present invention, it may be advantageous to use further emulsifiers. Thus, for example, the water resistance of the preparations according to the invention can be further increased. Suitable emulsifiers are, for example, alkylmethicone copolyols and alkyldimethicone copolyols, in particular cetyldimethicone copolyol, laurylmethicone copolyol, W/O emulsifiers, such as sorbitan stearate, glyceryl stearate, glycerol stearate, sorbitan oleate, lecithin, glyceryl isostearate, polyglyceryl-3 oleate, polyglyceryl-3 diisostearate, PEG-7-hydrogenated castor oil, polyglyceryl-4 isostearate, acrylate/$C_{10\text{-}30}$-alkyl acrylate cross-polymer, sorbitan isostearate, poloxamer 101, polyglyceryl-2 dipolyhydroxystearate, polyglyceryl-3 diisostearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate.

The O/W compositions according to the invention can advantageously comprise thickeners of the water phase. Advantageous thickeners are:
  Crosslinked or uncrosslinked acrylic acid or methacrylic acid homopolymers or copolymers. These include crosslinked homopolymers of methacrylic acid or acrylic acid, copolymers of acrylic acid and/or methacrylic acid and monomers which are derived from other acrylic or vinyl monomers, such as C10-30 alkyl acrylates, C10-30-alkyl methacrylates and vinyl acetate.

Thickening polymers of natural origin, for example based on cellulose, guar gum, xanthan, scleroglucan, gellan gum, rhamsan and karaya gum, alginates, maltodextrin, starch and its derivatives, carob seed flour, hylaronic acid, carrageenan.

Nonionic, anionic, cationic or amphoteric associative polymers, e.g. based on polyethylene glycols and their derivatives, or polyurethanes.

Crosslinked or uncrosslinked homopolymers or copolymers based on acrylamide or methacrylamide, such as homopolymers of 2-acrylamido-2-methylpropanesulfonic acid, copolymers of acrylamide or methacrylamide and methacryloyloxyethyltrimethylammonium chloride or copolymers of acrylamide and 2-acrylamido-2-methylpropanesulfonic acid.

Particularly advantageous thickeners are thickening polymers of natural origin, crosslinked acrylic acid or methacrylic acid homopolymers or copolymers and crosslinked copolymers of 2-acrylamido-2-methylpropanesulfonic acid.

Very particularly advantageous thickeners are xanthan gum, such as the products supplied under the names Keltrol® and Kelza® by CP Kelco or the products from RHODIA with the name Rhodopol, and guar gum, such as the products available under the name Jaguar® HP105 from RHODIA.

Very particularly advantageous thickeners are also crosslinked homopolymers of methacrylic acid or acrylic acid which are commercially available from Lubrizol under the names Carbopol® 940, Carbopol® 941, Carbopol® 980, Carbopol® 981, Carbopol® ETD 2001, Carbopol® EDT 2050, Carbopol® 2984, Carbopol® 5984 and Carbopol® Ultrez 10, from 3V under the names Synthalen® K, Synthalen® L and Synthalen® MS, and from PROTEX under the names Modarez® V 1250 PX, Modarez° V2000 PX, Viscaron® A1600 PE and Viscaron® A700 PE.

Very particular advantageous thickeners are crosslinked copolymers of acrylic acid or methacrylic acid and a $C_{10\text{-}30}$-alkyl acrylate or $C_{10\text{-}30}$-alkyl methacrylate and copolymers of acrylic acid or methacrylic acid and vinylpyrrolidone. Such copolymers are commercially available, for example, from Lubrizol under the names Carbopol® 1342, Carbopol® 1382, Pemulen® TR1 or Pemulen® TR2 and from ISP under the names Ultrathix P-100 (INCI: Acrylic Acid/VP Crosspolymer).

Very particular advantageous thickeners are crosslinked copolymers of 2-acrylamido-2-methylpropanesulfonic acid. Such copolymers are available, for example, from Clariant under the names Aristoflex® AVC (INCI: Ammonium Acryloyldimethyltaurate/VP Copolymer).

These thickeners are generally present in a concentration of from about 0% to 2% by weight, preferably 0% to 1% by weight, based on the total weight of the composition according to the invention.

Further compositions according to the invention may be water-in-oil or water-in-silicone emulsions. Preference is given to water-in-oil (W/O) or water-in-silicone emulsions (W/Si) which comprise one or more silicone emulsifiers (W/S) with an HLB value of ≤8 or one or more W/O emulsifiers with an HLB value of <7 and optionally one or more O/W emulsifiers with an HLB value of >10.

The silicone emulsifiers can advantageously be selected from the group comprising alkyldimethicone copolyols, such as, for example, cetyl PEG/PPG 10/1 dimethicone copolyol (ABIL® EM 90 from Goldschmidt AG) or lauryl PEG/PPG-18/18 dimethicones (Dow Corning® 5200 from Dow Corning Ltd.) and dimethicone copolyols, such as, for example, PEG-10 dimethicones (KF-6017 from Shin Etsu), PEG/PPG-18/18 dimethicones (Dow Corning 5225C from Dow Corning Ltd.) or PEG/PPG-19/19 dimethicones (Dow Corning BY-11 030 from Dow Corning Ltd.).

The W/O emulsifiers with an HLB value of <7 can advantageously be selected from the group comprising sorbitan stearate, sorbitan oleate, glyceryl isostearate, polyglyceryl-3 oleate, pentaerythrityl isostearate, methylglucose dioleate, PEG-7-hydrogenated castor oil, polyglyceryl-4 isostearate, hexyl laurate, sorbitan isostearate, polyglyceryl-2 dipolyhydroxystearate, polyglyceryl-3 diisostearate, PEG-30 dipolyhydroxystearate, diisostearoyl polyglyceryl-3 diisostearate, polyglyceryl-3 dipolyhydroxystearate, polyglyceryl-4 dipolyhydroxystearate, polyglyceryl-3 dioleate and wool wax alcohol (Eucerit).

The O/W emulsifiers with an HLB value of >10 can advantageously be selected from the group comprising lecithin, trilaureth-4 phosphate, polysorbate-20, polysorbate-60, PEG-22 dodecyl glycol copolymer, sucrose stearate and sucrose laurate.

An oil thickener can advantageously be used for stabilising the W/O emulsion according to the invention against sedimentation or flocculation of the water droplets.

Particularly advantageous oil thickeners are organomodified clays, such as organomodified bentonites (Bentone® 34 from Rheox), organomodified hectorites (Bentone® 27 and Bentone® 38 from Rheox) or organomodified montmorillonite, hydrophobic pyrogenic silica, where the silanol groups are substituted by trimethylsiloxy groups (AEROSIL® R812 from Degussa) or with dimethylsiloxy groups or polydimethylsiloxane (AEROSIL® R972, AEROSIL® R974 from Degussa, CAB-O-SIL® TS-610, "CAB-O-SIL® TS-720 from Cabot), magnesium or aluminium stearate, or styrene copolymers, such as, for example, styrene-butadiene-styrene, styrene-isopropene-styrene, styrene-ethylene/butene-styrene or styrene-ethylene/propene-styrene.

The thickener for the fatty phase can be present in an amount of from 0.1 to 5% by weight, based on the total weight of the emulsion, and better 0.4 to 3% by weight.

The aqueous phase can also comprise stabilizers. The stabilizer can be, for example, sodium chloride, magnesium chloride or magnesium sulphate and mixtures thereof.

Oils can be used in W/O, W/Si and O/W emulsions.

If present, the fatty phase of the composition according to the invention comprises at least one non-volatile oil. The fatty phase of the composition can in addition also comprise volatile oils and waxes. The O/W composition comprises advantageously 0 to 45% by weight of oils, based on the total weight of the composition, and particularly advantageously 0 to 20% by weight of oils. The W/O or W/Si composition advantageously comprises at least 20% by weight of oils, based on the total weight of the composition.

The non-volatile oil is advantageously selected from the group of mineral, animal, vegetable or synthetic origin, polar or nonpolar oils and mixtures thereof.

Polar oils can be selected from the lecithins and the fatty acid triglycerides, namely the triglycerol esters of saturated and/or unsaturated, branched and/or unbranched alkanecarboxylic acids of chain length from 8 to 24, in particular 12 to 18, carbon atoms. For example, the fatty acid triglycerides can be selected from the group of cocoglyceride, olive oil, sunflower oil, soybean oil, peanut oil, rapeseed oil, almond oil, palm oil, coconut oil, castor oil, wheat germ oil, grapeseed oil, safflower oil, evening primrose oil, macadamia nut oil, apricot kernel oil, avocado oil and the like.

Further advantageous polar oils can be selected from the group of esters of saturated and/or unsaturated, branched and/or unbranched alkanecarboxylic acids of chain length from 3 to 30 carbon atoms and saturated and/or unsaturated, branched and/or unbranched alcohols of chain length from 3 to 30 carbon atoms, and also from the group of esters of aromatic carboxylic acids and saturated and/or unsaturated, branched and/or unbranched alcohols of chain length from 3 to 30 carbon atoms. For example, the ester oils can preferably be selected from the group of phenethyl benzoate, octyl palmitate, octyl cocoate, octyl isostearate, octyldodeceyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, diisopropyl adipate, isooctyl stearate, isononyl stearate, isononyl isononanoate, 2-ethylhexyl palmitate, 2-ethylhexyl laurate, 2-hexyldecyl laurate, 2-hexyldecyl stearate, 2-octyldodecyl palmitate, 2-octyldodecyl myristate, 2-octyldodecyl lactate, 2-diethylhexyl succinate, diisostearyl malate, glyceryl triisostearate, diglyceryl triisostearate, stearyl heptanoate, oleyl oleate, oleyl erucate, erucyl oleate, erucyl erucate, tridecyl stearate, tridecyl trimellitate, and also synthetic, semisynthetic and natural mixtures of such esters, such as, for example, jojoba oil.

The polar oils can advantageously be selected from the group of dialkyl ethers and dialkyl carbonates, for example dicaprylyl ether (Cetiol® OE from Cognis) and/or dicaprylyl carbonate (for example Cetiol® CC from Cognis) are advantageous.

It is also preferred to select the polar oils from the group isoeicosane, neopentyl glycol diheptanoate, propylene glycol dicaprylate/dicaprate, caprylic/capric/diglyceiyl succinate, butylene glycol dicaprylate/dicaprate, $C_{12-13}$-alkyl lactate, di-$C_{12-13}$-alkyl tartrate, C12-15 alkyl benzoate, myristyl myristate, isodecyl neopentanoate, triisostearin, dipentaerythrityl hexacaprylate/hexacaprate, propylene glycol monoisostearate, tricaprylin, dimethyl isosorbide, butyloctylsalicylate (for example that available under the trade name Hallbrite® BHB from CP Hall), hexadecyl benzoate and butyloctyl benzoate and mixtures thereof (Hallstar® AB) and/or diethylhexyl naphthalate (Hallbrite® TQ or Corapan® TQ from Syrnrise).

The non-volatile oil can likewise advantageously also be a nonpolar oil which is selected from the group of branched and unbranched hydrocarbons, in particular mineral oil, vaseline oil, paraffin oil, squalane and squalene, polyolefins, for example polydecenes, hydrogenated polyisobutenes, C13-16 isoparaffin and isohexadecane.

The nonpolar nonvolatile oil can be selected among the non-volatile silicone oils.

Of the non-volatile silicone oils, the polydimethylsiloxanes (PDMS), which are optionally phenylated, such as phenyltrimethicone, or are optionally substituted with aliphatic and/or aromatic groups or with functional groups, for example hydroxyl groups, thiol groups and/or amino groups; polysiloxanes modified with fatty acids, fatty alcohols or polyoxyalkylenes and mixtures thereof can be given.

The composition according to the invention can also comprise a wax.

Within the context of the present specification, a wax is defined as a lipophilic fatty substance which is solid at room temperature (25° C.) and exhibits a reversible solid/liquid change in state at a melting temperature between 30° C. and 200° C. Above the melting point, the wax becomes low viscosity and miscible with oils.

The wax is advantageously selected from the groups of natural waxes, such as, for example, cotton wax, carnauba wax, candelilla wax, esparto wax, Japan wax, Montan wax, sugarcane wax, beeswax, wool wax, shellac, microwaxes, ceresine, ozokerite, ouricuri wax, cork fibre wax, lignit waxes, berry wax, shea butter or synthetic waxes, such as paraffin waxes, polyethylene waxes, waxes produced by Fischer-Tropsch synthesis, hydrogenated oils, fatty acid esters and glycerides which are solid at 25° C., silicone waxes and derivatives (alkyl derivatives, alkoxy derivatives, and/or esters of polymethylsiloxane) and mixtures thereof. The waxes can be present in the form of stable dispersions of colloidal wax particles which can be prepared by known processes, for example as in "Microemulsions Theory and Practice", L. M. Prince Ed., Academic Press (1977), pages 21-32.

Waxes may be present in amounts of from 0 to 10% by weight, based on the total weight of the composition, and preferably 0 to 5% by weight.

The composition according to the invention can also comprise a volatile oil which is selected from the group of volatile hydrocarbon oils, siliconised oils or fluorinated oils.

The volatile oil can be present in an amount of from 0 to 25% by weight, based on the total weight of the emulsion, preferably 0 to 20% by weight and even more preferably 0 to 15% by weight.

Within the context of the present specification, a volatile oil is an oil which, upon contact with the skin at room temperature and atmospheric pressure, evaporates in less than one hour. The volatile oil is liquid at room temperature and, at room temperature and atmospheric pressure, has a vapour pressure of from 0.13 to 40 000 Pa ($10^{-3}$ to 300 mm Hg), preferably 1.3 to 13 000 Pa (0.01 to 100 mm Hg) and particularly preferably 1.3 to 1300 Pa (0.01 to 10 mm Hg) and a boiling point of from 150 to 260° C. and preferably 170 to 250° C.

A hydrocarbon oil is understood as meaning an oil which is formed essentially from carbon atoms and hydrogen atoms and optionally oxygen atoms or nitrogen atoms and contains no silicon atoms or fluorine atoms, where it may also consist of carbon atoms and hydrogen atoms; however, it can also contain ester groups, ether groups, amino groups or amide groups.

A silicone oil is understood as meaning an oil which contains at least one silicon atom and in particular Si—O groups, such as, in particular, polydiorganosiloxanes.

A fluorinated oil is to be understood as meaning an oil which contains at least one fluorine atom.

The volatile hydrocarbon oil according to the invention can be selected from the hydrocarbon oils with a flash point of from 40 to 102° C., preferably 40 to 55° C. and even more preferably 40 to 50° C.

For example, the volatile hydrocarbon oils are those with 8 to 16 carbon atoms and mixtures thereof, in particular branched $C_{8-16}$-alkanes, such as the isoalkanes (which are also referred to as isoparaffins) with 8 to 16 carbon atoms, isododecane, isodecane, isohexadecane and, for example, the oils which are supplied under the tradenames Isopars® or Permetyls®; and the branched $C_{8-16}$-esters, such as isohexyl neopentanoate and mixtures thereof.

The volatile hydrocarbon oils such as isododecane, isodecane and isohexadecane are particularly advantageous.

The volatile siliconised oil according to the invention can be selected from the siliconised oils with a flash point of from 40 to 102° C., preferably a flash point above 55° C. and at most 95° C. and particularly preferably in the range from 65 to 95° C.

For example, the volatile siliconised oils are straight-chain or cyclic silicone oils having 2 to 7 silicon atoms, where these silicones optionally contain alkyl or alkoxy groups having 1 to 10 carbon atoms.

The volatile siliconised oils such as octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof are particularly advantageous.

The volatile fluorinated oil generally has no flash point.

For example, the volatile fluorinated oils are nonafluoroethoxybutane, nonafluoromethoxybutane, decafluoropentane, tetradecafluorohexane, dodecafluoropentane and mixtures thereof.

The preferred cosmetic acceptable medium of the composition according to the invention comprises water and optionally a cosmetically compatible water-miscible suitable organic solvent.

The water used in the composition according to the invention may be a blossom water, pure demineralised water, mineral water, thermal water and/or seawater.

In the case of an O/W composition as composition according to the invention, the water fraction can be in the range from 40 to 95% by weight, preferably in the range from 50 to 90% by weight, very particularly in the range from 60 to 80% by weight, based on the total weight of the composition. In the case of a W/O composition, the water fraction is in the range from 0 to 60% by weight, preferably in the range from 10 to 50% by weight, very preferably in the range from 30 to 50% by weight, based on the total weight of the composition.

The preferred solvents are, for example, the aliphatic alcohols with C1-4 carbon atoms, such as ethanol and isopropanol; polyol and derivatives thereof, such as propylene glycol, dipropylene glycol, butylene-1,3 glycol, polypropylene glycol, glycol ethers such as alkyl (C1-4) ethers of mono-, di- or tripropylene glycol or mono-, di- or triethylene glycol, and mixtures thereof.

The quantitative fraction of the solvent or solvents in the composition according to the invention can be, for example, in the range from 0 to 25% by weight and preferably 0 to 15% by weight, based on the total weight of the composition.

Further compositions according to the invention may be a loose powder or a compact powder.

The decorative cosmetic composition according to the invention can preferably also provide a so-called foundation effect, by means of which unevennesses in the skin, such as wrinkles etc., are smoothed.

The decorative cosmetic compositions according to the invention can comprise further additives which are customary in cosmetics, such as, for example, antioxidants, photoprotective agents and/or other auxiliaries and additives, such as, for example, emulsifiers, interface-active substances, antifoams, thickeners, surfactants, active ingredients, humectants, sensory additive, UV filters, film formers, solvents, coalescing agents, aroma substances, odour absorbers, perfumes, gel formers and/or other polymer dispersions, such as, for example, dispersions based on polyacrylates, fillers, softeners, pigments, flow agents and/or thixotropic agents, suppleness agents, preservatives. The amounts of the various additives are known to the person skilled in the art for the range to be used and are, for example, in the range from 0 to 25% by weight, based on the total weight of the composition.

The decorative cosmetic composition according to the invention can also comprise sensory additives. Sensory additives are to be understood as meaning colourless or white, mineral or synthetic, lamellar, spherical or elongated inert particles or a nonparticulate sensory additive which, for example, further improve the sensory properties of the formulations and, for example, leave behind a velvety or silky skin feel.

The sensory additives can be present in the composition according to the invention, for example, in an amount of from 0 to 10% by weight, based on the total weight of the composition, and preferably from 0 to 7%.

Advantageous particulate sensory additives within the context of the present invention are talc, mica, silicon dioxide, kaolin, starch and derivatives thereof (for example tapioca starch, distarch phosphate, aluminium and sodium starch octenyl succinate and the like), pyrogenic silica, pigments which have neither primarily a UV-filter effect nor colouring effect (such as e.g. boron nitride etc.), boron nitride, calcium carbonate, dicalcium phosphate, magnesium carbonate, magnesium hydrogencarbonate, hydroxyapatites, microcrystalline cellulose, powders of synthetic polymers, such as polyamides (for example the polymers available under the trade name "Nylon®"), polyethylene, poly-β-alanine, polytetrafluoroethylene ("Teflon®"), polyacrylate, polyurethane, lauroyl-lysine, silicone resin (for example the polymers available under the trade name "Tospearl®" from Kobo Products Inc.), hollow particles of polyvinylidene/aciylonitriles (Expancel® from Akzo Nobel) or hollow particles of silicon oxide (Silica Beads® from MAPRECOS).

Advantageous nonparticulate sensory additives can be selected from the group of dimethiconols (e.g. Dow Corning 1503 Fluid from Dow Corning Ltd.), silicone copolymers (e.g. divinyldimethicone/dimethicone copolymer, Dow Corning HMW 2220 from Dow Corning Ltd.) or silicone elastomers (e.g. dimethicone crosspolymer, Dow Corning 9040 Silicone Elastomer Blend from Dow Corning Ltd.).

The composition according to the invention can optionally also comprise sun protection filters, where the total amount of the sun protection filters is 0% by weight to 30% by weight, advantageously 0% by weight to 20% by weight, particularly advantageously 0% by weight to 10% by weight, based on the total weight of the composition according to the invention. The sun protection filters (or UV filters) can in particular be selected from the organic filters, the physical filters and mixtures thereof.

The composition according to the invention can comprise UV-A filters, UV-B filters or broadband filters. The UV filters used can be oil-soluble or water-soluble. The list of specified UV filters below is of course not limiting.

Examples of the UV-B filters are:
(1) salicylic acid derivatives, particularly homomethyl salicylate, octyl salicylate and 4-isopropylbenzyl salicylate;
(2) cinnamic acid derivatives, in particular 2-ethylhexyl p-methoxycinnamate, which is available from Givaudan under the name Parsol MCX® and isopentyl 4-methoxycinnamate;
(3) liquid β,β'-diphenylacrylate derivatives, in particular 2-ethylhexyl α,β'-diphenylacrylate or octocrylene, which is available from BASF under the name UVINUL N539®;
(4) p-aminobenzoic acid derivatives, in particular 2-ethylhexyl 4-(dimethylamino)benzoate, amyl 4-(dimethylamino)benzoate;
(5) 3-benzylidenecamphor derivatives, in particular 3-(4-methylbenzylidene)camphor which is commercially available from Merck under the name EUSOLEX 6300®, 3-benzylidenecamphor, benzylidenecamphor sulphonic acid and polyacrylamidomethyl benzylidenecamphor;
(6) 2-phenylbenzimidazole-5-sulphonic acid, which is available under the name EUSOLEX 232® from Merck;
(7) 1,3,5-triazine derivatives, in particular: -2,4,6-tris[p-(2'-ethylhexyl-1'-oxycarbonyl)anilino]-1,3,5-triazine, which is supplied by BASF under the name UVINUL T150®, and -dioctylbutamidotriazone, which is supplied by Sigma 3V under the name UVASORB HEB®;
(8) esters of benzalmalonic acid, in particular di(2-ethylhexyl) 4-methoxybenzalmalonate and 3-(4-(2,2-bisethoxycarbonylvinyl)phenoxy)propenyl)methoxysiloxane/dimethylsiloxane copolymer, which is available from Roche Vitamines under the name Parsol® SLX; and
(9) the mixtures of these filters.

Examples of UV-A filters are:
(1) dibenzoylmethane derivatives, particularly 4-(t-butyl)-4'-methoxydibenzoylmethane, which is supplied by Givaudan under the name PARSOL 1789® and 1-phenyl-3-(4'-isopropylphenyl)propane-1,3-dione;
(2) benzene-1,4-[di(3-methylidenecamphor-10-sulphonic acid)], optionally complete or partially neutralised, commercially available under the name MEXORYL SX® from Chimex
(3) hexyl 2-(4'-diethylamino-2'-hydroxybenzoyl)benzoate (also aminobenzophenone);
(4) silane derivatives or polyorganosiloxanes with benzophenone groups;
(5) anthranilates, particularly menthyl anthranilate, which is supplied by Symrise under the name NEO HELIOPAN MA®;
(6) compounds which contain at least two benzoazolyl groups or at least one benzodiazolyl group per molecule, in particular 1,4-bis-benzimidazolylphenylene-3,3',5,5'-tetrasulphonic acid and its salts, which are commercially available from Symrise;
(7) silicon derivatives of benzimidazolylbenzazoles, which are N-substituted, or of benzofuranylbenzazoles, in particular: -2-[1-[3-[1,3,3,3-tetramethyl-1-[(trimethylsilyl)oxy]disiloxanyl]propyl]-1H-benzimidazol-2-yl]benzoxazole; -2-[1-[3-[1,3,3,3-tetramethyl-1-[(trimethylsilyl)oxy]disiloxanyl]propyl]-1H-benzimidazol-2-yl]-benzothiazole; -2-[1-(3-trimethylsilanylpropyl)-1H-benzimidazol-2-yl]-benzoxazole; -6-methoxy-1,1'-bis(3-trimethylsilanylpropyl)1H,1'H-[2,2']dibenzimidazolylbenzoxazole; 2-[1-(3-trimethylsilanylpropyl)-1H-benzimidazol-2-yl]benzothiazole; which are described in the patent application EP-A-1 028 120;
(8) triazine derivatives, in particular 2,4-bis-[5-1(dimethylpropyl)benzoxazol-2-yl-(4-phenyl)imino]-6-(2-ethylhexyl)imino-1,3,5-triazine, which is supplied by 3V under the name Uvasorb®K2A; and
(9) mixtures thereof.

Examples of broadband filters are:
(1) benzophenone derivatives, for example 2,4-dihydroxybenzophenone (benzophenone-1); 2,2',4,4'-tetrahydroxybenzophenone (benzophenone-2);

2-hydroxy-4-methoxybenzophenone (benzophenone-3), available from BASF under the name UNIVNUL M40®;

2-hydroxy-4-methoxybenzophenone-5-sulphonic acid (benzophenone-4), and its sulphonate form (benzonphenone-5), commercially available from BASF under the name UVINUL MS40®;

2,2'-dihydroxy-4,4'-dimethoxybenzophenone (benzophenone-6-);

5-chloro-2-hydroxybenzophenone (benzophenone-7-);

2,2'-dihydroxy-4-methoxybenzophenone (benzophenone-8);

the disodium salt of 2,2'-dihydroxy-4,4'-dimethoxybenzophenone-5,5'-disulphonic acid (benzophenone-9-);

2-hydroxy-4-methoxy-4'-methylbenzophenone (benzophenone-10);

benzophenone-11;

2-hydroxy-4-(octyloxy)benzophenone (benzophenone-12).

(2) triazine derivatives, in particular 2,4-bis{[4-2-ethylhexyloxy)-2-hydroxy]-phenyl}-6-(4-methoxyphenyl)-1,3,5-triazine, which is supplied by Ciba Geigy under the name TINOSORB S®, and 2,2'-methylenebis[6-(2H-benzotriazol-2-yl)4-(1,1,3,3-tetramethylbutyl) phenol], which is available from Ciba Geigy under the name TINOSORB M®; and (3) 2-(1H-benzotriazol-2-yl)-4-methyl-6-[2-methyl-3-[1,3,3,3-tetramethyl-1-[(trimethylsilyl)oxy]disiloxanyl] propyl]phenol with the INCI name Drometrizole Trisiloxane.

It is also possible to use a mixture of two or more filters and a mixture of UV-B filters, UV-A filters and broadband filters, and also mixtures with physical filters.

Of the physical filters, the sulphate of barium, oxides of titanium (titanium dioxide, amorphous or crystalline in the form of rutile and/or anatase), of zinc, of iron, of zirconium, of cerium, silicon, manganese or mixtures thereof may be given. The metal oxides can be present in particle form with a size in the micrometer range or nanometer range (nanopigments). The average particle sizes for the nanopigments are, for example, 5 to 100 nm.

The decorative cosmetic composition according to the invention can comprise one or more (humectants) moisturisers.

Particularly advantageous moisturisers within the context of the present invention are, for example, glycerol, polyglycerol, sorbitol, dimethyl isosorbide, lactic acid and/or lactates, in particular sodium lactate, butylene glycol, propylene glycol, biosaccaride gum-1, glycine soya, hydroxyethylurea, ethylhexyloxyglycerol, pyrrolidonecarboxylic acid and urea. In addition, it is especially advantageous to use polymeric moisturisers from the group of water-soluble and/or water-swellable and/or water-gelable polysaccharides. For example, hyaluronic acid, chitosan and/or a fucose-rich polysaccharide, which is available under the name Fucogel™ 1000 from SOLABIA S.A., are especially advantageous.

Within the context of the present invention, water-soluble antioxidants can be used particularly advantageously, such as, for example, vitamins, e.g. ascorbic acid and derivatives thereof. Vitamin E and derivatives thereof, and also vitamin A and derivatives thereof are very particularly advantageous.

Further advantageous active ingredients in the composition according to the invention are α-hydroxy acid, such as glycolic acid, lactic acid, malic acid, tartaric acid, citric acid and mandelic acid, β-hydroxy acid, such as salicylic acid, and acylated derivatives thereof, 2-hydroxyalkanoic acid and its derivatives; natural active ingredients and/or derivatives thereof, such as, for example, alpha-lipoic acid, folic acid, phytoene, D-biotin, coenzyme Q10, alpha-glucosylrutin, carnitine, carnosine, natural and/or synthetic isoflavonoids, creatine creatinine, taurine and/or [beta]-alanine and also 8-hexadecene-1,16-dicarboxylic acid (dioic acid, CAS number 20701-68-2; provisional INCI name Octadecenedioic acid) and/or Licochalcon A and the plant extracts.

Advantageous film formers are trimethylsiloxysilicates, silicon acrylate copolymers (e.g. TIB4-200 from Dow Corning or KP-561 from Shin Etsu), trimethylpentaphenyl trisiloxane (Dow Corning 555 Cosmetic Fluid from Dow Corning Ltd.) or vinylpyrrolidone copolymer (e.g. PVP/eicosene copolymer or PVP/hexadecane copolymer).

The present invention is illustrated by reference to examples, although these are not to be understood as being limiting. Unless stated otherwise, all of the quantitative data, fractions and percentages are based on the weight and the total amount or on the total weight of the compositions.

EXAMPLES

Unless indicated otherwise, all of the percentages are based on the weight.

Unless noted otherwise, all of the analytical measurements refer to measurements at temperatures of 23° C.

The solids or solid-body contents are determined by heating a weighed sample at 125° C. to constant weight. At constant weight, the solid-body content is calculated by reweighing the sample.

Unless expressly mentioned otherwise, NCO contents were determined volumetrically in accordance with DIN-EN ISO 11909.

The control on free NCO groups was carried out by means of IR spectroscopy (band at 2260 $cm^{-1}$)

The stated viscosities were determined by means of rotary viscometry in accordance with DIN 53019 at 23° C. using a rotary viscometer from Anton Paar Germany GmbH, Ostfildern, Germany.

The average particle sizes (the number-average is given) of the polyurethane dispersions were determined following dilution with deionised water by means of laser correlation spectroscopy (instrument: Malvern Zetasizer 1000, Malver Inst. Limited).

Substances Used And Abbreviations

Diaminosulphonate: $NH_2—CH_2CH_2—NH—CH_2CH_2—SO_3Na$ (45% strength in water)

Desmophen® 2020/C2200: Polycarbonate polyol, OH number 56 mg of KOH/g, number-average molecular weight 2000 g/mol (Bayer MaterialScience AG, Leverkusen, Germany)

PolyTHF® 2000: Polytetramethylene glycol polyol, OH number 56 mg of KOH/g, number-average molecular weight 2000 g/mol (BASF AG, Ludwigshafen, Germany)

PolyTHF® 1000: Polytetramethylene glycol polyol, OH number 112 mg of KOH/g, number-average molecular weight 1000 g/mol (BASF AG, Ludwigshafen, Germany)

Polyether LB 25: monofunctional polyether based on ethylene oxide/propylene oxide of number-average molecular weight 2250 g/mol, OH number 25 mg of KOH/g (Bayer MaterialScience AG, Leverkusen, Germany)

Example 1

Polyurethane Dispersion 1

987.0 g of PolyTHF® 2000 (component A2)), 375.4 g of PolyTHF® 1000 (component A2)), 761.3 g of Desmophen®

C2200 (component A2)) and 44.3 g of polyether LB 25 (component A4)) were heated to 70° C. in a standard stirring apparatus. Then, a mixture of 237.0 g of hexamethylene diisocyanate (component A1)) and 313.2 g of isophorone diisocyanate (component A1)) was added and the mixture was stirred at 120° C. until the theoretical NCO value was reached. The finished prepolymer was dissolved with 4830 g of acetone and in so doing cooled to 50° C., and then a solution of 25.1 g of ethylenediamine (component B1)), 116.5 g of isophoronediamine (component B1)), 61.7 g of diaminosulphonate (component B2)) and 1030 g of water was metered in. The afterstirring time was 10 min. The mixture was then dispersed by adding 1250 g of water. The solvent was removed by distillation in vacuo.

The resulting white dispersion had the following properties:
Solids content: 61%
Particle size (LCS): 312 nm
Viscosity (viscometer, 23° C.): 241 mPas
pH (23° C.): 7.15

Example 2

Polyurethane Dispersion 2

450 g of PolyTHF® 1000 (component A2)) and 2100 g of PolyTHF® 2000 (component A2)) were heated to 70° C. Then, a mixture of 225.8 g of hexamethylene diisocyanate (component A1)) and 298.4 g of isophorone diisocyanate (component A1)) was added and the mixture was stirred at 100-115° C. until the actual NCO value had dropped below the theoretical NCO value. The finished prepolymer was dissolved with 5460 g of acetone at 50° C. and then a solution of 29.5 g of ethylenediamine (component B1)), 143.2 g of diaminosulphonate (component B2)) and 610 g of water was metered in. The afterstirring time was 15 min. The mixture was then dispersed by adding 1880 g of water. The solvent was removed by distillation in vacuo and a storage-stable dispersion was obtained.
Solids content: 56%
Particle size (LCS): 276 nm
Viscosity: 1000 mPas Example 3

Polyurethane Dispersion 3

1649.0 g of a polyester of adipic acid, hexanediol and neopentyl glycol with an average molecular weight of 1700 g/mol (component A2)) were heated to 65° C. Then, 291.7 g of hexamethylene diisocyanate (component A1)) were added and the mixture was stirred at 100-115° C. until the actual NCO value had dropped below the theoretical NCO value. The finished prepolymer was dissolved with 3450 g of acetone at 50° C. and then a solution of 16.8 g of ethylenediamine (component B1)), 109.7 g of diaminosulphonate (component B2)) and 425 g of water was metered in. The afterstirring time was 15 min. The mixture was then dispersed by adding 1880 g of water. The solvent was removed by distillation in vacuo and a storage-stable dispersion was obtained.
Solids content: 42%
Particle size (LCS): 168 nm
Viscosity: 425 mPas
pH: 7.07

Example 4

Polyurethane Dispersion 4

340 g of a polyester of adipic acid, hexanediol and neopentyl glycol with an average molecular weight of 1700 g/mol (component A2)) were heated to 65° C. Then, 60.1 g of hexamethylene diisocyanate (component A1)) were added and the mixture was stirred at 105° C. until the actual NCO value had dropped below the theoretical NCO value. The finished prepolymer was dissolved with 711 g of acetone at 50° C. and then a solution of 2.1 g of ethylenediamine (component B1)), 32.4 g of diaminosulphonate (component B2)) and 104.3 g of water was metered in. The afterstirring time was 15 min. The mixture was then dispersed by adding 1880 g of water. The solvent was removed by distillation in vacuo and a storage-stable dispersion was obtained.
Solids content: 40%
Particle size (LCS): 198 nm
Viscosity: 700 mPas
pH: 6.31

Example 5

Polyurethane Dispersion 5

450 g of PolyTHF® 1000 (component A2)) and 2100 g of PolyTHF® 2000 (component A2)) were heated to 70° C. Then, a mixture of 225.8 g of hexamethylene diisocyanate (component A1)) and 298.4 g of isophorone diisocyanate (component A1)) was added and the mixture was stirred at 100-115° C. until the actual value had dropped below the theoretical NCO value. The finished prepolymer was dissolved with 5460 g of acetone at 50° C. and then a solution of 351 g of diaminosulphonate (component B2)) and 610 g of water was metered in. The afterstirring time was 15 min. The mixture was then dispersed by adding 1880 g of water. The solvent was removed by distillation in vacuo and a storage-stable dispersion was obtained.
Solids content: 40%
Viscosity: 1370 mPas Examples of Cosmetic Formulations:

| a) Mascara | |
|---|---|
| Raw materials | % by wt. (based on the cosmetic composition) |
| Isododecane | 20.00 |
| D5 Cyclomethicone | 5.00 |
| Carnauba Wax | 6.00 |
| Trimethyl Siloxysilicate | 0.75 |
| Dimethicone 200/200 | 10.00 |
| Polyurethane according to the invention (based on solid in the polyurethane dispersion) | 3.0 |
| Ceresine Wax SP252 | 3.00 |
| Paraffin Wax 130/135 | 3.50 |
| Polyethylene | 2.50 |
| Nylon-12 | 2.00 |
| Silica | 2.00 |
| Stearic Acid | 1.00 |
| Bentone Gel in Isododecane | 15.00 |
| Phenoxyethanol | 1.00 |
| Black Iron Oxide LC989 EM | 10.00 |
| White Beeswax | 1.75 |
| Deionized Water | ad 100 | a) Mascara

| Raw materials | % by wt. (based on the cosmetic composition) |
|---|---|
| Magnesium Aluminium Silicate | 0.50 |
| Triethanolamine 99% | 0.90 |
| Net-DTB (10% in Butylene Glycol) | 1.00 | b) Foundation

| Raw materials | % by wt. (based on the cosmetic composition) |
|---|---|
| Deionized Water | ad 100 |
| Cellulose Gum | 0.30 |
| Magnesium Aluminium Silicate | 0.35 |
| Lecithin | 0.40 |
| Triethanolamine 99% | 1.25 |
| Butylene Glycol | 6.00 |
| Titanium Dioxide (Water Dispersible) | 8.00 |
| Red Iron Oxide | 0.40 |
| Yellow Iron Oxide | 0.80 |
| Black Iron Oxide | 0.10 |
| Colloidal Kaolin | 2.00 |
| Methyl Paraben | 0.20 |
| Isoeicosane | 10.00 |
| Isostearic Acid | 1.00 |
| Stearic Acid | 2.50 |
| Glyceryl Stearate | 1.50 |
| Tridecyl Trimellitate | 1.00 |
| Glyceryl Stearate SE | 1.00 |
| Propyl Paraben | 0.20 |
| Polyurethane according to the invention (based on solid in the polyurethane dispersion) | 5.0 |
| Active ingredients | q.s. |
| Dyes | q.s. |
| Perfume | q.s. |
| Preservative | q.s. |
| Aqua | ad 100 | c) Eyeliner

| Raw materials | % by wt. (based on the cosmetic composition) |
|---|---|
| Oleyl Alcohol | 0.5 |
| Propylene Glycol | 7.5 |
| Xanthan Gum | 0.1 |
| Silica | 0.1 |
| Polyurethane according to the invention (based on solid in the polyurethane dispersion) | 2.0 |
| Active ingredients | q.s. |
| Dyes | q.s. |
| Perfume | q.s. |
| Preservative | q.s. |
| Aqua | ad 100 | d) Tanning composition

| Raw materials | % by wt. (based on the cosmetic composition) |
|---|---|
| Dihydroxyacetone | 3.0 |
| Glycerol | 8.0 |
| Cetyl Alcohol | 0.5 |
| Silica | 3.0 |
| Methylglucose Sesquistearate | 2.0 |
| PEG-100 stearate | 1.0 |
| Cyclomethicone | 4.0 |
| Polyurethane according to the invention (based on solid in the polyurethane dispersion) | 2.0 |
| Octyldodecanol | 3.0 |
| Dicaprylyl carbonate | 2.0 |
| EDTA | 1.0 |
| Xanthan Gum | 0.3 |
| Sodium Citrate | 0.4 |
| Citric acid | 0.3 |
| Vitamin E acetate | 0.5 |
| Active ingredients | q.s. |
| Dyes | q.s. |
| Perfume | q.s. |
| Preservative | q.s. |
| Aqua | ad 100 | e) Tinted daycream

| Raw materials | % by wt. (based on the cosmetic composition) |
|---|---|
| Glyceryl Stearate Citrate | 3.5 |
| Octyldodecanol | 3.0 |
| Cyclomethicone | 3.0 |
| Cetearyl Alcohol | 1.5 |
| Squalane | 2.0 |
| Shea butter | 5.0 |
| Carbomer | 0.5 |
| Glycerol | 10.0 |
| 4-Methylbenzylidene Camphor | 5.0 |
| Octyl Methoxycinnamate | 2.5 |
| Octocrylene | 6.0 |
| Butylmethoxydibenzoylmethane | 2.5 |
| Polyurethane according to the invention (based on solid in the polyurethane dispersion) | 5.0 |
| EDTA | 1.0 |
| Active ingredients | q.s. |
| Dyes | q.s. |
| Perfume | q.s. |
| Preservative | q.s. |
| Aqua | ad 100 | f) Lipstick

| Raw materials | % by wt. (based on the cosmetic composition) |
|---|---|
| Ricinus oil | 3.0 |
| Caprylic/Capric Triglycerides | 3.0 |
| Octyldodecanol | 5.0 |
| Hydrogenated polyisobutene | 3.0 |
| Jojaba oil | 1.0 |
| Lanolin oil | 1.0 |
| PEG 45/Dodecyl Glycol copolymer | 2.0 |
| Polyglyceryl-3 Diisostearate | 2.4 |
| Cetyl palmitate | 1.0 |
| C20-40 Alkyl Stearate | 8.0 |
| Carnauba wax | 2.0 |
| Microcrystalline wax | 8.0 |
| Glycerol | 10.0 |
| Polyurethane according to the invention (based on solid in the polyurethane dispersion) | 15.0 |
| Active ingredients | q.s. |
| Dyes | q.s. | f) Lipstick

| Raw materials | % by wt. (based on the cosmetic composition) |
| --- | --- |
| Perfume | q.s. |
| Preservative | q.s. |
| Aqua | ad 100 |

Comparative Experiment:

The polyurethanes according to the invention are compared with PVP/eicosene copolymer (formulation according to the table below) in a mascara formulation.

| Raw materials | % by wt. (based on the cosmetic composition) | |
| --- | --- | --- |
| | 1 | 2 |
| Isododecane | 20.00 | 20.00 |
| D5 Cyclomethicone | 5.00 | 5.00 |
| Carnauba Wax | 6.00 | 6.00 |
| Trimethyl Siloxysilicate | 0.75 | 0.75 |
| Dimethicone 200/200 | 10.00 | 10.00 |
| PVP/Eicosene Copolymer | 7.50 | |
| Polyurethane from Example 3 | | 3.0 |
| Ceresine Wax SP252 | 3.00 | 3.00 |
| Paraffin Wax 130/135 | 3.50 | 3.50 |
| Polyethylene | 2.50 | 2.50 |
| Nylon-12 | 2.00 | 2.00 |
| Silica | 2.00 | 2.00 |
| Stearic Acid | 1.00 | 1.00 |
| Bentone Gel in Isododecane | 15.00 | 15.00 |
| Phenoxyethanol | 1.00 | 1.00 |
| Black Iron Oxide LC989 EM | 10.00 | 10.00 |
| White Beeswax | 1.75 | 1.75 |
| Deionized Water | ad 100 | ad 100 |
| Magnesium Aluminum Silicate | 0.50 | 0.50 |
| Triethanolamine 99% | 0.90 | 0.90 |
| Net-DTB (10% in Butylene Glycol) | 1.00 | 1.00 |

200 μm films of the formulations described above are drawn onto a glass plate at 35° C. The films are left to dry for 24 h at 30° C. To measure the water resistance, the glass plates are dipped into a waterbath at RT with stirring for 4 hours. The water resistance is proportional to the film area which remains.

Results of the comparison of the mascara formulation described above with a formulation according to the invention as in Example 3:

| Raw materials | % by wt. (based on the cosmetic composition) | |
| --- | --- | --- |
| | 1 | 2 |
| Film former | PVP/Eicosene copolymer | Polyurethane from Example 3 |
| Area which remains (%) | 20 | 100 |
| Water resistance | poor | excellent |

The invention claimed is:

1. A decorative cosmetic composition comprising at least one polyurethane, wherein the decorative composition comprises 0.1 to 20% by weight of the at least one polyurethane, and wherein the decorative composition is face make-up, blusher, rouge, mascara, eyeliner, kohl pencil, eye shadow, lipstick, or lipgloss, and one or more constituents, which produce a coloring, a glitter, and/or a metallic effect, wherein the at least one polyurethane is obtainable by reacting one or more water-insoluble,
non-water-dispersible, isocyanate-functional polyurethane prepolymers A) with two or more amino-functional compounds B),
wherein the two or more amino-functional compounds B) include at least one amino-functional compound B2), which has ionic and/or ionogenic groups, and an amino-functional compound B1), which has no ionic and/or ionogenic group,
wherein the decorative cosmetic composition provides color-imparting, glitter-imparting, and/or metallic-imparting effect on skin and/or hair,
wherein the composition is in the form of oil-in-water, water-in-oil, water-in-silicone oil, silicone oil-in-water, oil-in-water-in-oil, or water-in-oil-in-water emulsions, and
wherein the isocyanate-functional polyurethane prepolymers A) are prepared from
A1) organic polyisocyanates, which are selected from aliphatic, aromatic or cycloaliphatic polyisocyanates with an NCO functionality of greater than or equal to 2,
A2) polymeric polyols with number-average molecular weights of from 400 to 8000 g/mol, which is determined by gel permeation chromatography relative to polystyrene standard in tetrahydrofuran at 23° C., and OH functionalities of 1.5 to 6, and which are selected from one or more of the group consisting of polyether polyols, polycarbonate polyols, polyether-polycarbonate polyols, and polyester polyols,
A3) optionally hydroxy-functional compounds with molecular weights of 62 to 399 g/mol, and
A4) optionally nonionic hydrophilizing agents,
wherein the amino-functional compounds B) are selected from primary and/or secondary diamines.

2. The decorative cosmetic composition according to claim 1, wherein the isocyanate-functional polyurethane prepolymers A) are prepared from
A1) organic polyisocyanates, which are selected from aliphatic, aromatic or cycloaliphatic polyisocyanates with an NCO functionality of greater than or equal to 2,
A2) polymeric polyols with number-average molecular weights of from 400 to 8000 g/mol, which is determined by gel permeation chromatography relative to polystyrene standard in tetrahydrofuran at 23° C., and OH functionalities of 1.5 to 6, and which are selected from one or more of the group consisting of polyether polyols, polycarbonate polyols, polyether-polycarbonate polyols, and polyester polyols,
A3) optionally hydroxy-functional compounds with molecular weights of 62 to 399 g/mol, and
A4) the nonionic hydrophilizing agents.

3. The decorative cosmetic composition according to claim 2, wherein the nonionic hydrophilizing agents are polyoxyalkylene ethers having isocyanate- reactive hydroxyl groups.

4. The decorative cosmetic composition according to claim 1, wherein the nonionic hydrophilizing agents are polyoxyalkylene ethers having isocyanate-reactive hydroxyl groups.

5. The decorative cosmetic composition according to claim 1, wherein the two or more amino-functional compounds B) include ethylenediamine and diaminosulphonate.

6. A cosmetic method for producing a decorative effect on skin and optionally hair, comprises
applying a composition consisting of
at least one polyurethane,
one or more constituents, which produce a coloring, a glitter, and/or a metallic effect to the skin and optionally hair,
wherein the polyurethane is obtainable by reacting one or more water-insoluble, non-water-dispersible, isocyanate-functional polyurethane prepolymers A) with two or more amino-functional compounds B),
wherein the two or more amino-functional compounds B) include at least one amino-functional compound B2), which has ionic and/or ionogenic groups, and an amino-functional compound B 1), which has no ionic and/or ionogenic group,
wherein the decorative effect is color-imparting, glitter-imparting and/or metallic-imparting,
wherein the one or more constituents comprise a dye,
wherein the composition is in the form of oil-in-water, water-in-oil, water-in-silicone oil, silicone oil-in-water, oil-in-water-in-oil, or water-in-oil-in-water emulsions, and
wherein the isocyanate-functional polyurethane prepolymers A) are prepared from
A1) organic polyisocyanates, which are selected from aliphatic, aromatic or cycloaliphatic polyisocyanates with an NCO functionality of greater than or equal to 2,
A2) polymeric polyols with number-average molecular weights of from 400 to 8000 g/mol, which is determined by gel permeation chromatography relative to polystyrene standard in tetrahydrofuran at 23° C., and OH functionalities of 1.5 to 6, and which are selected from one or more of the group consisting of polyether polyols, polycarbonate polyols, polyether-polycarbonate polyols, and polyester polyols,
A3) optionally hydroxy-functional compounds with molecular weights of 62 to 399 g/mol, and
A4) optionally nonionic hydrophilizing agents, wherein the amino-functional compounds B) are selected from primary and/or secondary diamines,
optionally moisturisers, water, solvents, waxes, stabilizers, antioxidants, photoprotective agents, emulsifiers, humectants, sensory additives, UV filters, polymer dispersions based on polyacrylates, pigments, and combinations thereof.

7. The cosmetic method according to claim 6, wherein the polyurethane contains at least one sulphonic acid and/or sulphonate group.

8. The cosmetic method according to claim 6, wherein the method comprises application of the composition to the skin, wherein the composition at least partially remains on it.

9. The cosmetic method according to claim 6 wherein the amino-functional compound B2) is 2-(2-aminoethylamino) ethanesulphonic acid and/or salts thereof.

10. The cosmetic method according to claim 6, wherein the amino-functional compound B1) is a diamine which has no ionic and/or ionogenic groups.

11. The cosmetic method according to claim 6, wherein the polyurethane contains at least one sodium sulphonate group.

12. The cosmetic method according to claim 6, wherein the composition comprises 0.1 to 20% by weight of the polyurethane.

13. The cosmetic method according to claim 6, wherein the dye is selected from the group consisting of lipophilic dyes, hydrophilic dyes, pigments, and mother of pearl.

14. The cosmetic method according to claim 6, wherein the composition comprises 1 to 30% by weight of the dye.

15. The cosmetic method according to claim 6, wherein the composition is face make-up, tinted skin cream, blusher, rouge, mascara, eyeliner, kohl pencil, eye shadow, lipstick, or lipgloss.

16. The cosmetic method according to claim 6, wherein the isocyanate-functional polyurethane prepolymers A) are prepared from
A1) organic polyisocyanates, which are selected from aliphatic, aromatic or cycloaliphatic polyisocyanates with an NCO functionality of greater than or equal to 2,
A2) polymeric polyols with number-average molecular weights of from 400 to 8000 g/mol, which is determined by gel permeation chromatography relative to polystyrene standard in tetrahydrofuran at 23° C., and OH functionalities of 1.5 to 6, and which are selected from one or more of the group consisting of polyether polyols, polycarbonate polyols, polyether-polycarbonate polyols, and polyester polyols,
A3) optionally hydroxy-functional compounds with molecular weights of 62 to 399 g/mol, and
A4) the nonionic hydrophilizing agents.

17. The cosmetic method according to claim 16, wherein the nonionic hydrophilizing agents are polyoxyalkylene ethers having isocyanate-reactive hydroxyl groups.

18. The cosmetic method according to claim 6, wherein the two or more amino-functional compounds B) include ethylenediamine and diaminosulphonate.

* * * * *